US007231242B2

(12) United States Patent
Degim et al.

(10) Patent No.: US 7,231,242 B2
(45) Date of Patent: Jun. 12, 2007

(54) METHOD FOR MEASURING BLOOD UREA LEVEL BY REVERSE IONTOPHORESIS

(76) Inventors: Tuncer Degim, Gazi Universitesi Eczacilik Fak., Farmasotik Teknoloji Ana Bilim Dali, Etiler, 06330, Ankara (TR); Sibel Ilbasmis, Gazi Universitesi Eczacilik Fak., Farmasotik Teknoloji Ana Bilim Dali, Etiler, 06330, Ankara (TR); Zelihagul Degim, Gazi Universitesi Eczacilik Fak., Farmasotik Teknoloji Ana Bilim Dali, Etiler, 06330, Ankara (TR); Rusen Dundaroz, G.A.T.A. Acil T p Anabilim Dal, Etlik. 06018, Ankara (TR); Metin Denli, Genelkurmay Saglik Komutan Yrd., Kizilay, 06330, Ankara (TR)

( * ) Notice: Subject to any disclaimer, the term of this patent is extended or adjusted under 35 U.S.C. 154(b) by 0 days.

(21) Appl. No.: 10/510,779

(22) PCT Filed: Apr. 8, 2003

(86) PCT No.: PCT/TR03/00032

§ 371 (c)(1),
(2), (4) Date: Jul. 11, 2005

(87) PCT Pub. No.: WO03/084604

PCT Pub. Date: Oct. 16, 2003

(65) Prior Publication Data

US 2005/0273045 A1 Dec. 8, 2005

(30) Foreign Application Priority Data

Apr. 8, 2002 (TR) ................ a 2002 00942

(51) Int. Cl.
*A61B 5/05* (2006.01)
(52) U.S. Cl. .............. 600/361; 600/345; 600/354; 600/364; 600/348
(58) Field of Classification Search ............. 600/306, 600/309, 345–397
See application file for complete search history.

(56) References Cited

U.S. PATENT DOCUMENTS

| | | | | |
|---|---|---|---|---|
| 5,279,543 A * | 1/1994 | Glikfeld et al. | ............... | 604/20 |
| 5,591,123 A * | 1/1997 | Sibalis et al. | ............... | 604/20 |
| 5,771,890 A * | 6/1998 | Tamada | ............... | 600/347 |
| 5,908,400 A * | 6/1999 | Higo et al. | ............... | 604/20 |
| 6,144,869 A * | 11/2000 | Berner et al. | ............... | 600/347 |
| 6,643,544 B1 * | 11/2003 | Adachi et al. | ............... | 604/20 |

* cited by examiner

*Primary Examiner*—Charles Marmor
*Assistant Examiner*—Navin Natnithithadha
(74) *Attorney, Agent, or Firm*—Robert L. Epstein; Epstein Drangel Bazerman & James, LL

(57) ABSTRACT

A method for measuring and determining urea level in human blood by reverse iontophoresis comprising the following steps of:
  placing an anode electrode on skin,
  placing a container comprising a solution including urease and a cathode electrode on skin,
  applying electric current to the anode electrode and the cathode electrode so that an electrical circuit is established there between, whereby urea molecules migrate from blood into the container,
  determining the urea level in the blood by the changes in the pH of the urease solution.

10 Claims, 5 Drawing Sheets

METHOD FOR MEASURING BLOOD UREA LEVEL BY REVERSE IONTOPHORESIS

FIELD OF THE INVENTION

The invention relates to a method for measuring urea level in human blood by reverse iontophoresis and a device—urea meter—using the method and in particular, the amount of urea level is determined by the changes of pH of the urease containing solution so as to predict the blood urea level.

BACKGROUND OF THE INVENTION

Measurement and determination of urea level is particularly important for patients with insufficient kidney function, neonates, pregnant women, or for the epidemiological screening.

Various attempts have been observed for measuring and determining urea level in human blood, including biological-based methods and sampling of human blood.

These conventionally utilized methods offer some reasonable outcomes in the sense of determining urea level in human blood. However, as it is acknowledged by a person skilled in the art, these practices accompany with some disadvantages comprising microbiological contamination, embolism as well as causing pain to the patient, since these exercised methods are associated with taking biologic or blood samples and subsequently analyzing these samples so as to determine the urea level in the blood.

The risks involved are not limited with the present practices as set forth above, since taking blood samples is particularly important for patients with diabetes, hemophilia or some coagulation disorders and more particularly the hemophiliacs.

Further disadvantages with the present practices apply for neonates and infants with regard to the risk of infection and the difficulty for performing such taking blood samples from the neonates and infants.

As for epidemiological screening for uremia, there exists possibility of mixing up the samples/injectors and thus lead to a greater infectious contamination.

Yet another disadvantage with the existing practices is obvious for pregnant women, since taking blood thereof also poses additional discomfort and difficulty.

Patients with uremia are influenced both emotionally and physically due to giving blood samples frequently for undergoing subsequent dialysis.

DESCRIPTION OF RELATED ART

Proposed invention relates to reverse ionophotoresis. Such a method has been in use for example in WO 03000340 disclosing a method for non-invasively determining the relative levels of two substances present in a biological system includes the steps of extracting by reverse iontophoresis charged and uncharged substances from said biological system.

WO 03000340 solely discloses the use of reverse ionophotoresis for a biological system and does not teach or suggest any method for measuring and determining the urea level in human blood.

WO 030100538 discloses a method and a device for increasing reverse iontophoresis flux so that non-invasive extraction of uncharged and charged permanent molecules alike through the skin.

Therefore WO 03010538 does not suggest a solution for measuring and determining urea level in human blood.

Iontophoresis usage is known from various applications as shown in the following reference list to pass some compounds through the human skin or to enhance the permeability. Reverse iontophoresis however, is utilized for taking glucose from the blood to measure the blood glucose level.

REFERENCES

1—Tierney M. J., Tamada J. A., Potts R. O., Jovanovic L. Garg S. Clinical evaluation of the GlucoWatch® biographer: a continual, non-invasive glucose monitor for patients with diabetes, Biosensons & Bioelectronics 16 (2001) 621–629.

2—Brunner, G. A., Ellmerer, M., Sendlhofer, G., et al., 1998. Validation of home blood glucose meters with respect to clinical and analytical approaches. Diab. Care 21 (4) 585–590.

3—Cambiaso, A., Delfino, L., Grattarola, M., Verreschi, G., Ashworth, D., Maines, A., et al., 1996. Modelling and simulation of a diffusion limited glucose biosensor. Sens. Act. B. 33, 203–207.

4—Tierney, M. J., Tamada, J. A., Potts, R. O., et al. 2000. The Gluco-Watch biogra r: a frequent automatic, and non-invasive glucose monitor. Ann. Med. 32, 632–641.

5—Zhang, Y., Hu., Y., Wilson, G. W., Moatti-Sirat, D., Poitout, V., Reach, G., 1994. Elimination of the acetaminophen interference in an implantable glucose sensor. Anal. Chem. 66, 1183–1188.

6—Clarke, W. L., Cox, D., Gonder-Frederick, L. A., Carter, W., Pohl, S. I., 1987. Evaluating clinical accuracy of systems for self-monitoring of blood glucose. Diab. Care 10 (5) 622–628. Denning, W. E. 1943. Statistical Adjustment of Data. Wiley, New York.

7—Garg, S. K., Potts, R. O., Cakerman, N. R., Fermi, S. J., Tarnada, J. A., Chase, H. P., 1999. Correlation of fingerstick blood glucose measurements with GlucoWatch biographer glucose results in young subjects with type 1 diabetes. Diab. Care 22, 1708–1714.

8—Ginsberg, B. H., 1992. An overview of minimally invasive technologies. Clin. Chem., 38, 1596–1600.

9—Kilpatrick, E. S., McLeod, M. J., Rubley, A. G., Small, M., 1994. A ward comparison between the One Touch II and Glucometer II blood glucose meters. Diab. Med. 11, 214–217.

10—Kurrik, R. T., Oliver, J. J., Waterhouse, S. R., Dunn, T., Jayalakshimi, Y., Lesho, M., et al., 1999. Application of the mixtures of experts algorithm for signal processing in a noninvasive glucose monitoring system. Sens. Act. B. 60, 2–8.

BRIEF SUMMARY OF THE INVENTION

The object of the present invention is to measure and determine urea level in human blood securely and without involving any contamination risk.

Another object of the present invention is o measure and determine urea level in human blood painlessly.

Yet further object of the present invention is to monitor of urea level in human blood.

With this proposed invention, the urea level can be obtained in a very short period of time without taking blood or any other biological samples from the patient.

In iontophoresis procedure, by using an electrical current (producing an electrical gradient), the ions (molecules or atoms having a net charge or partially charged) can be carried to the other side of the membrane according to applied current and electrical charge and it is possible to control by iontophoresis. Electrodes or similar tools are provided to the both side of the membrane and the applied electrical current or potential (direct or alternative current, square, sinus or triangular or even different frequencies and/or currencies) can be applied as needed.

The ions in the solution migrate according to their charges and their movement is in proportional to the current. For instance, positively charged ions migrate to the negative electrode side and vice versa. While the charged ions are migrating according to the electrical current, they also drag the uncharged molecules along with themselves. At this instance, traveling from one side to the other side of the membrane creates a flow, a turbulence occurs (this is so called an electro-osmotic flow). Therefore the unchanged particles (atoms/molecules) can also be able to pass through the membrane by being pulled into this vortex or into the motion and this passage occurs at a much faster rate than that of passive diffusion.

DETAILED DESCRIPTION OF THE INVENTION

Figure 1:
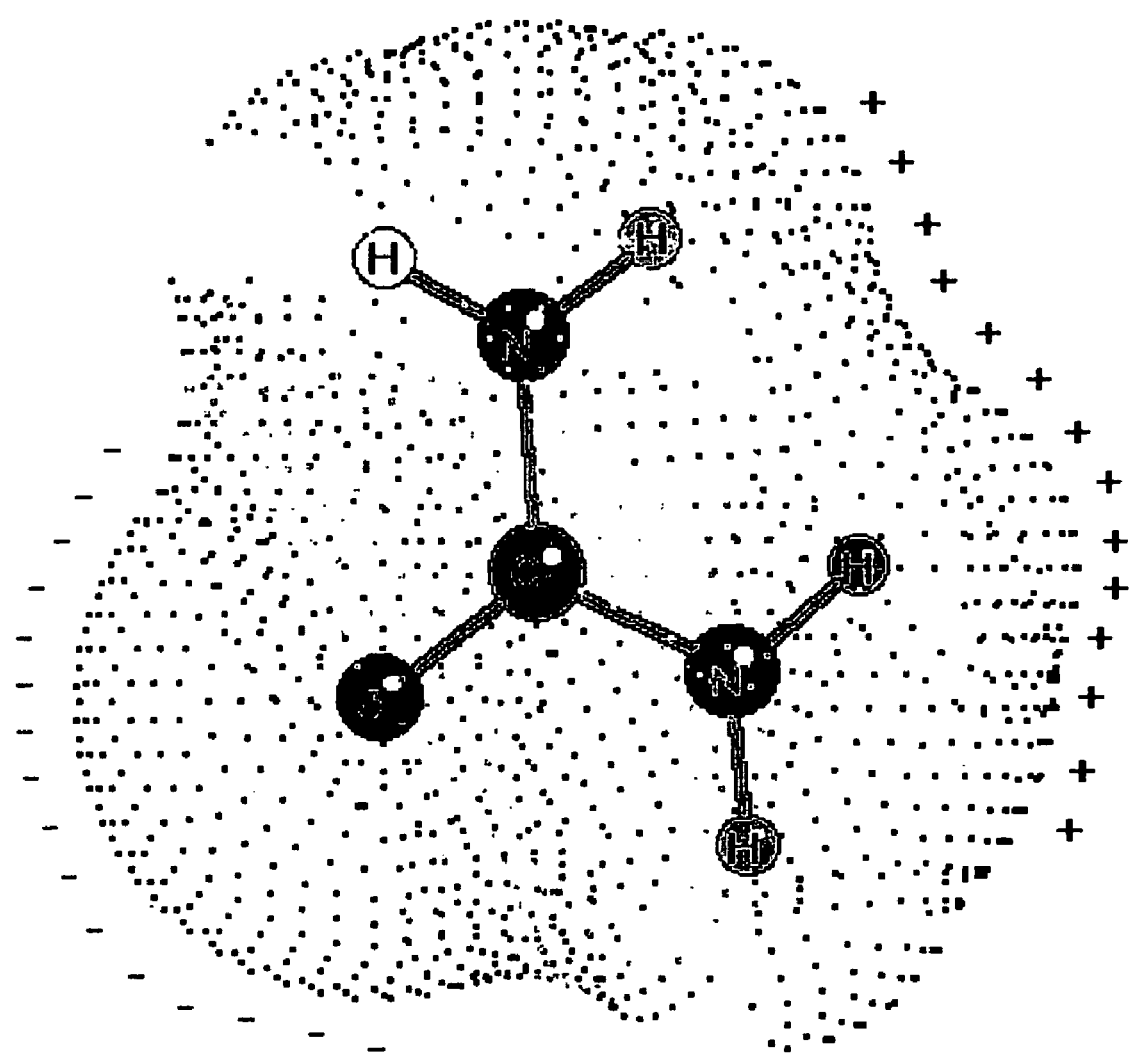
FIG. 1 is a representation of the analytical structure of urea.
Figure 2:
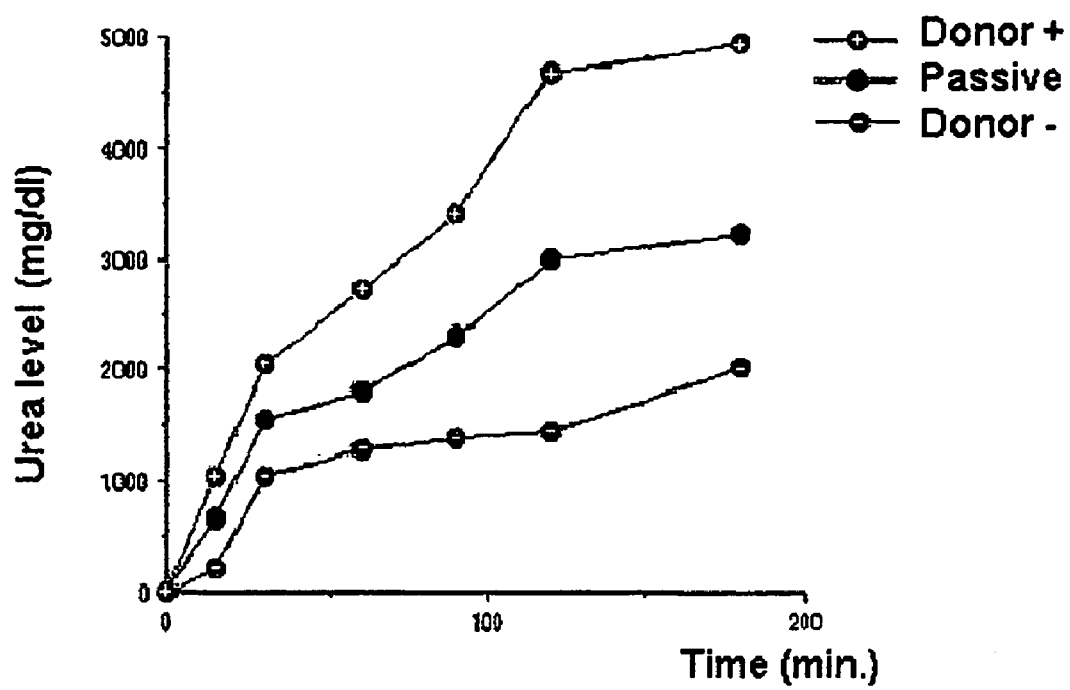
FIG. 2 is a graphical representation of the degree of urea transportation under different conditions.

When the molecular structure of urea investigated as in FIG. 1, although it is known to behave as not charged molecules, it is seen that some local charges are present on the molecule. According to the experiments conducted, the higher urea transportation was observed than passive diffusion when urea was present at the positive electrode side because of the positive local charges on the molecule as in FIG. 2. There is also a possibility that the electro-osmotic flow was partially influential for this transfer. However, during the transfer, with the other small but charged ions like potassium and sodium are present in the solution, the transfer rate decreases, but still the transfer is much larger and faster than the passive diffusion.

Figure 3:
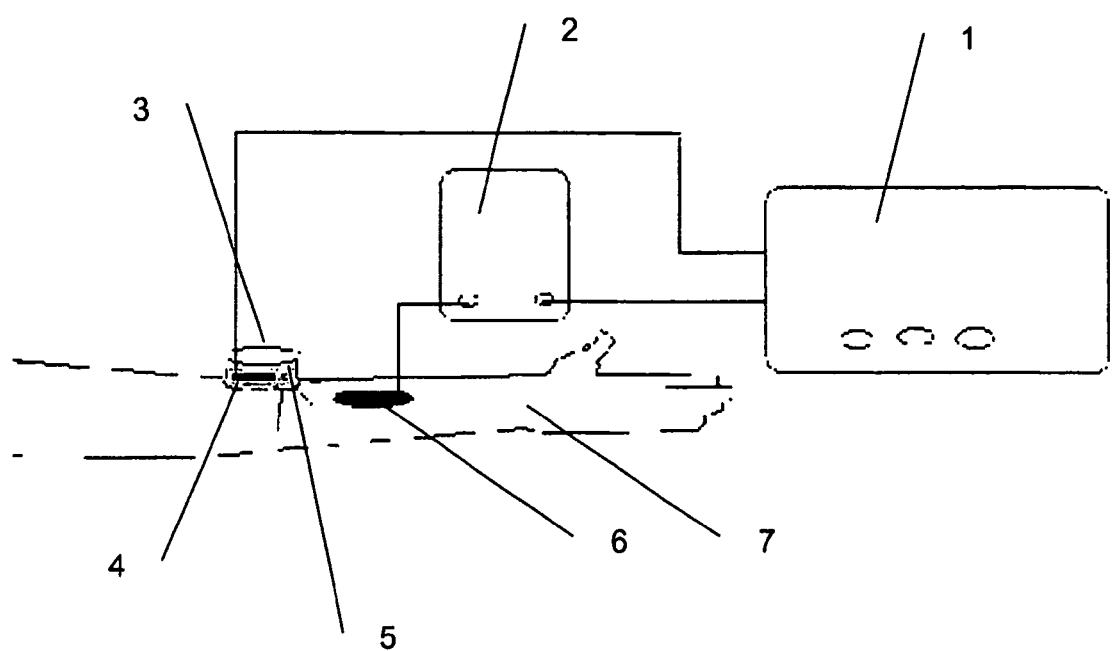
FIG. 3 is a graphical representation of the practice of the present invention.

These experiments were repeated using human skin (7) as the membrane, and similar results were obtained. So, since the urea molecules are partially charged with + load the reverse-iontophoresis can be applied. For this, an anode, (+) electrode (6), can be placed right on the skin (7) surface in the forearm, and near this place, a cathode (4), (−) electrode is inserted into a container (3) which contains an isotonic saline solution (5). When the electrical current is applied by a power supplier (1), the urea molecules will migrate from blood to the container (3) on the outside (FIG. 3). This will be in direct proportion to the current and area used.

In experiments conducted, 10 ml isotonic saline solution has been placed into the container (3). The area of the Container is 12.5 cm². The current is supplied with a 1000 uA, measured by an ampere-meter (2), level and applied for 5 minutes. After the current is terminated the values in the solution are measured. These experiments have been conducted on volunteers as is explained above with the reverse iontophoresis procedure and the solution (5) in the container (3) in which urea is accumulated is taken and the amount of urea in this solution is determined.

Figure 4:
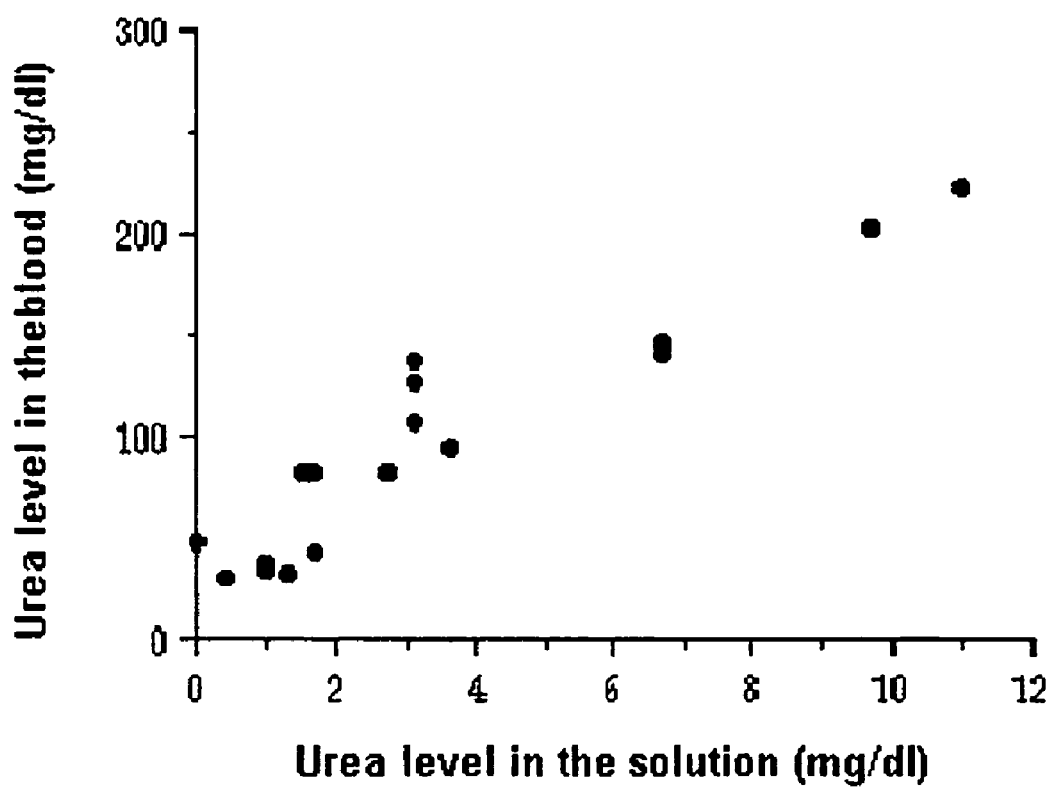
FIG. 4 is a graphical representation of the relationship between the urea level in the blood and the urea level in the analytic solution.

The levels of urea in this solution were analyzed in biochemistry laboratory using urease method. In the process of this analysis, after adding a reactive agent, the ultraviolet absorbency at 305 nm is measured. The measured absorbency values placed into the calibration equation and the urea levels have been measured in 'mg/d' terms. When the blood urea levels and the results obtained by reverse iontophoresis procedure are compared, (when all else like current, surface and time period held constant), it has been observed that there has been a definite relationship in between the two methods (FIG. 4).

Figure 5:
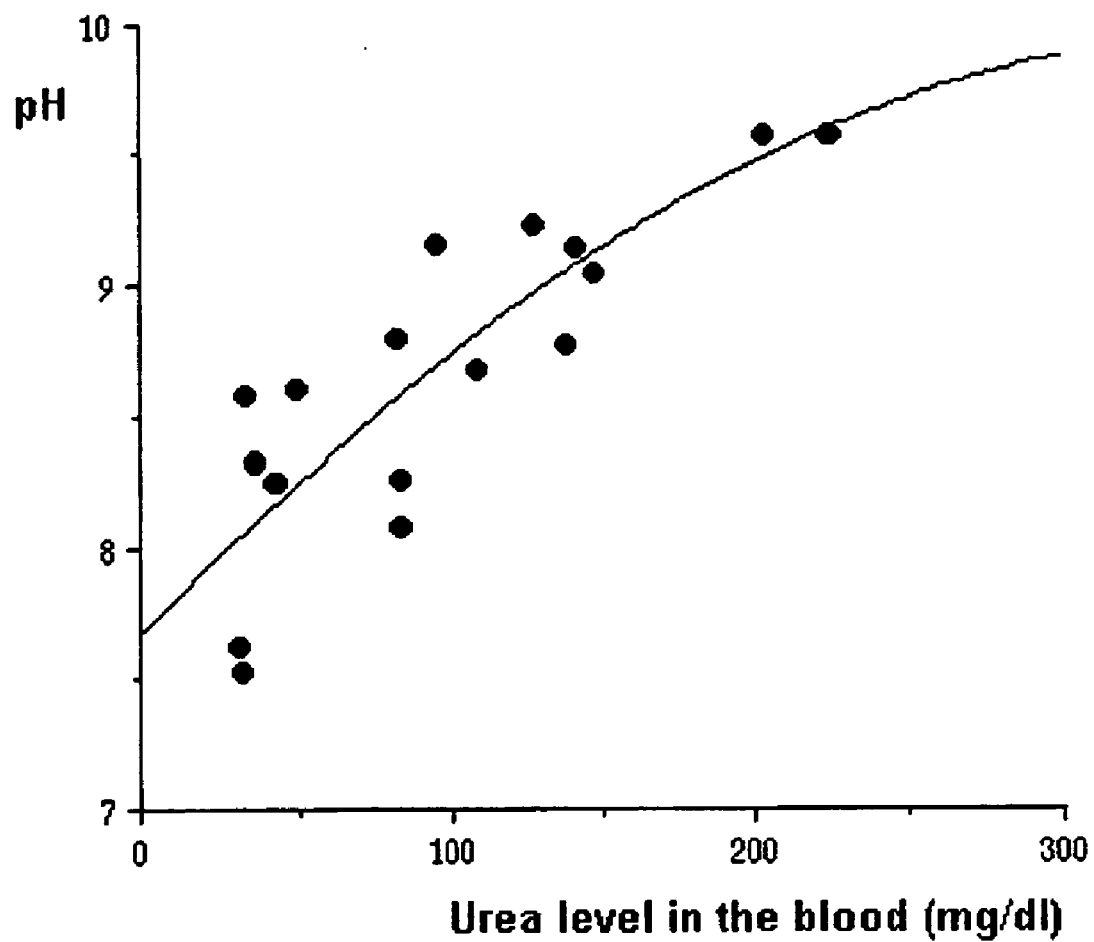
FIG. 5 is a graphical representation of the relationship between the urea level in the blood and the pH of the analytic solution.

In this proposed system, the amount of urea drawn into the solution (5) is measured-calculated according to the change of pH induced by the urease. Urease is an enzyme specific to urea. When it comes across with urea, $NH_3$ is produced, and it raises the pH value of the solution. This is directly related with the amount of urea. One ml of 1% urease in the isotonic saline solution is added into the 5 ml of solution obtained form the reverse iontophoresis procedure (which contains urea drawn through the patient's skin). After 10 minutes, the mixture-new solution's pH is measured. The relationship between the patient's blood urea level and the pH values obtained in our experiment is shown in FIG. 5. In the experiments, the composition of the electrodes is Ag for the anode and AgCl for the cathode. These electrodes do not cause any pH level change, but other electrodes can also be used such as copper, vanadium, steel, gold, etc.

Alternatively, determination of urea level in solution is performed by measuring thereof through using spectrophotometric methods or by determining the change in the electrical properties of the skin in replace of the above-mentioned determination of change in pH.

The method in the scope of the present invention is performed by practicing on a device i.e. an arm watch-like device or might be called as a urea-meter. The urea watch comprises a (+) electrode (6), and a solution (5) containing NaCl and urease in the inside of the watch casing-container (3) being in touch with the skin surface (7). The watch further comprises a dialysis membrane which protects from any leakage of the solution and provides the transfer of urea through (this membrane can be a hemodyalysis membrane). There is also a (−) electrode (4) at the other side of the skin (7) which can be mounted at the strap of the watch, the pH measurement and the batteries must be present to provide a current.

In an alternative embodiment, the possibility of using a gel comprising a collection medium instead of solution mentioned above can be utilized. There is also a microcomputer (micoprocessor) and the software for the measurement of the urea level in blood and the pre-calibrated pH values and can be indicated the urea level in blood.

While but a limited number of embodiments have been here specifically disclosed, it will be apparent that the invention has a broader scope as defined in the appended claims.

We claim:

1. A device for determining from a contact area on a patient's skin the urea level in the patient's blood, which comprises: a housing designed to be secured to a patient's limb; an anode; a container including a cathode, an exterior, a solution including urease, and a membrane operatively interposed between said solution and the exterior of the said container, wherein said anode and said membrane being capable of making contact with the patient's skin; means for applying a potential difference between said anode and said cathode so as to produce reverse iontophoresis to cause urea molecules to migrate to said container; means for determining the pH of the solution before and after said potential difference has been applied; and means for measuring the urea level in the patient's blood based on the change of the pH of the solution.

2. The device of claim 1, in which said container also contains an isotonic saline solution.

3. The device of claim 1, in which said container contents are in the form of a gel.

4. The device of claim 2, in which said container contents are in the form of a gel.

5. The method of determining from a contact area on the patient's skin the urea level in the patient's blood which comprises (a) placing on the skin at said contact area an anode and a container containing a cathode and a solution including urease and having a dialysis membrane adapted to be operatively interposed between said solution and said contact area, (b) applying a potential difference between said anode and said cathode so as to produce reverse iontophoresis to cause urea molecules to migrate into said container, and (c) measuring the urea level in the patient's blood by determining the change in pH of said urease before and after said potential difference has been applied.

6. The method of claim 5, in which said solution includes an isotonic saline solution.

7. The method of claim 5, in which said solution is in the form of a gel.

8. The method of claim 6, in which said solution is in the form of a gel.

9. In the method of claim 6, using a software controlled microcomputer for determining the urea level in the patient's blood.

10. The method of claim 5, in which the anode, the container with its contents, and means for applying said potential difference are embodied into a limb-attachable wristwatch-like device.

* * * * *